US012427221B2

(12) United States Patent
Gal et al.

(10) Patent No.: US 12,427,221 B2
(45) Date of Patent: Sep. 30, 2025

(54) ELECTRONICALLY CONTROLLED SCENT PRODUCTION

(71) Applicant: iRoma Scents A.B. Ltd., Herzliya (IL)

(72) Inventors: Avner Gal, Herzliya (IL); Uzi Malimovka, Givat Shmuel (IL); Eugene Naidis, Ashkelon (IL); Alexander Molotsky, Holon (IL)

(73) Assignee: iRoma Scents A.B. Ltd., Herzliya (IL)

( * ) Notice: Subject to any disclaimer, the term of this patent is extended or adjusted under 35 U.S.C. 154(b) by 0 days.

(21) Appl. No.: 18/727,298

(22) PCT Filed: Dec. 20, 2022

(86) PCT No.: PCT/IL2022/051351
§ 371 (c)(1),
(2) Date: Jul. 8, 2024

(87) PCT Pub. No.: WO2023/119275
PCT Pub. Date: Jun. 29, 2023

(65) Prior Publication Data
US 2024/0399014 A1 Dec. 5, 2024

Related U.S. Application Data

(60) Provisional application No. 63/265,729, filed on Dec. 20, 2021.

(51) Int. Cl.
*A61L 9/12* (2006.01)
*A61L 9/14* (2006.01)

(52) U.S. Cl.
CPC ................ *A61L 9/125* (2013.01); *A61L 9/14* (2013.01); *A61L 2209/134* (2013.01)

(58) Field of Classification Search
CPC ....... A61L 9/125; A61L 9/14; A61L 2209/134
See application file for complete search history.

(56) References Cited

U.S. PATENT DOCUMENTS

| 4,142,650 A | * | 3/1979 | Almouli | B65D 83/386 |
| | | | | 222/402.11 |
| 7,610,118 B2 | | 10/2009 | Schramm et al. | |

(Continued)

FOREIGN PATENT DOCUMENTS

| KR | 101173541 B1 | 8/2012 |
| WO | 2009006851 A1 | 1/2009 |

(Continued)

OTHER PUBLICATIONS

International Search Report for PCT/IL2022/051351, dated Mar. 29, 2023. International Searching Authority Israel Patent Office Jerusalem, Israel.

(Continued)

*Primary Examiner* — Sean E Conley
*Assistant Examiner* — Brendan A Hensel
(74) *Attorney, Agent, or Firm* — M&B IP Analysts, LLC

(57) ABSTRACT

Electronically controlled scent producer includes: a body, having plurality of chambers and actuators, each chamber receiving a respective scent essence, each actuator respective of a chamber and having actuator port, a first motor and second motor, and a local control unit, responsive of scent emission instructions configured to selectively activate second motor to displace body, to align a selected actuator port of an actuator respective of the selected chamber with a nozzle of a housing, and to selectively activate first motor to induce emission of the scent essence contained in selected chamber through selected actuator port, so as to produce a scent emission directed to external environment through nozzle. Activation of scent producer may be initiated according to scent track linked to audio/visual presentation, the scent track including scent emission instructions with timing information and associated scent identification information, (Continued)

such that predetermined scent emitted during a respective scene of presentation.

18 Claims, 8 Drawing Sheets

(56) References Cited

U.S. PATENT DOCUMENTS

| | | | |
|---|---|---|---|
| 7,837,065 B2* | 11/2010 | Furner | B05B 12/12 239/70 |
| 10,814,028 B2 | 10/2020 | Becker et al. | |
| 2016/0107186 A1 | 4/2016 | Chao et al. | |
| 2018/0369442 A1 | 12/2018 | Kelsen | |
| 2019/0263527 A1 | 8/2019 | Fantuzzi et al. | |
| 2020/0147256 A1* | 5/2020 | Nguyen | H04B 5/77 |
| 2020/0276353 A1* | 9/2020 | Juving-Brunet | A61L 9/122 |
| 2023/0285623 A1 | 9/2023 | Jones et al. | |

FOREIGN PATENT DOCUMENTS

| | | |
|---|---|---|
| WO | 2011021980 A1 | 2/2011 |
| WO | 2023119275 A1 | 6/2023 |

OTHER PUBLICATIONS

Written Opinion of the International Searching Authority for PCT/IL2022/051351, dated Mar. 29, 2023. International Searching Authority Israel Patent Office Jerusalem, Israel.

International Search Report for PCT/IB2024/058056, dated Oct. 31, 2024. Searching Authority, Israel Patent Office, Jerusalem, Israel.

Written Opinion of the Searching Authority for PCT/IB2024/058056, dated Oct. 31, 2024. Searching Authority, Israel Patent Office, Jerusalem, Israel.

* cited by examiner

ELECTRONICALLY CONTROLLED SCENT PRODUCTION

FIELD OF THE INVENTION

The present invention relates generally to the controlled production and emission of scents.

BACKGROUND OF THE INVENTION

In the field of performance venues, particularly in a movie theatre or home theatre setting, the watching experience could be improved by providing scents associated with the appropriate scenes of the movie to the audience.

There is thus a need for an improved system for scent delivery which can be used in connection with a performance venue, such as a movie theatre.

SUMMARY OF THE INVENTION

In accordance with one aspect of the present invention, there is thus provided an electronically controlled scent producer. The scent producer includes a moveable body, and a housing, configured to encase the body and including a nozzle extending therethrough. The body includes: a plurality of chambers; a plurality of actuators, respective of the chambers; a first motor; a second motor; and a local control unit. The chambers are disposed along a base on the interior of the body, each of the chambers configured to receive a respective scent essence. Each of the actuators includes an actuator port, configured to be aligned in a selected direction in relation to the body. The first motor is configured to drive the application of pressure in a selected actuator so as to induce emission of a scent essence through the actuator port. The second motor is configured to drive the displacement of at least a portion of the body. The local control unit, responsive of scent emission instructions, is configured to selectively activate the second motor to displace the body, so as to align with the nozzle a selected actuator port of an actuator respective of the selected chamber, and configured to selectively activate the first motor to induce emission of the scent essence contained in the selected chamber through the selected actuator port, so as to produce a scent emission directed to the external environment through the nozzle. The scent producer may further include a plurality of valves, each of the valves configured to dispense a scent essence into a respective one of the chambers. The scent producer may further include a cam, coupled to the first motor; a push member; a rocker; and a piston, where the first motor is driven so as to rotate the cam to drive the piston via the push member and the rocker, so as to depress the selected actuator to force at least a portion of the scent essence in the respective chamber to exit via the selected actuator port. The chambers may be disposed radially about a longitudinal axis of the body. The scent producer may further include a plurality of receptacles, each one of the receptacles associated with a respective chamber and to receive a respective actuator, where each of the actuators comprises a respective fin, and each of the receptacles comprises a respective slot, the respective fin configured to engage within a respective slot so as to maintain a direction of the respective actuator port. The housing may include a cover, and a shell, whereby the cover is configured to engage securely with the shell so as to encase the body, and where the nozzle extends through a wall of the cover, providing a pathway thereto from the selected actuator port to the external environment. The scent producer may further include a tray, where the body is secured to the tray and configured to rotate within the shell of the housing, in response to activation of the second motor. The chambers may be separated by a respective radial wall extending from an inner band to an inner wall of the base, each of the inner band and the inner wall describing a substantially circular band at a predetermined radial distance from a longitudinal axis of the body, the radial distance of the inner wall being greater than the radial distance of the inner band. The body may be a circular body, where the second motor is a rotation motor configured to rotate the chambers, so as to align the selected actuator port of the selected actuator respective of the selected chamber, with the nozzle. The body may be a linear body, where the second motor is configured to translate the chambers, so as to align the selected actuator port of the selected actuator respective of the selected chamber, with the nozzle. The local control unit may be configured to receive a scent track, associated with an audio/visual presentation, the scent track including the scent emission instructions including scent identification information and associated timing information, the local control unit configured to trigger an activation of the scent producer to emit at least one scent according to the scent track, by selectively activating the second motor and the first motor in response to the scent track, such that at least one predetermined scent is emitted during a respective scene of the presentation. The scent track may be received from at least one of: ta film projection system; a video broadcast system; a television; a set-top box; a streaming media player; a computing device; an audio medium source; a visual medium source; and/or a live performance.

In accordance with another aspect of the present invention, there is thus provided a system for generating timing and location coordinated scents linked to an audio/visual presentation. The system includes at least one electronically controlled scent producer, positioned in proximity to a user of the presentation. The scent producer includes a moveable body, and a housing, configured to encase the body and including a nozzle extending therethrough. The body includes: a plurality of chambers; a plurality of actuators, respective of the chambers; a first motor; a second motor; and a local control unit. The chambers are disposed along a base on the interior of the body, each of the chambers configured to receive a respective scent essence. Each of the actuators includes an actuator port, configured to be aligned in a selected direction in relation to the body. The first motor is configured to drive the application of pressure in a selected actuator so as to induce emission of a scent essence through the actuator port. The second motor is configured to drive the displacement of at least a portion of the body. The local control unit, responsive of scent emission instructions, is configured to selectively activate the second motor to displace the body, so as to align with the nozzle a selected actuator port of an actuator respective of the selected chamber, and configured to selectively activate the first motor to induce emission of the scent essence contained in the selected chamber through the selected actuator port, so as to produce a scent emission directed to the external environment through the nozzle. The system further includes a central control unit, communicatively coupled with the local control unit. The central control unit is configured to transmit to the scent producer a scent track associated with the presentation, the scent track including scent emission instructions including scent identification information and associated timing information, and configured to initiate an activation of the scent producer in response to the scent track, to emit at least one scent according to the scent emission instructions, such that at least one predetermined scent is emitted to the user during a respective scene of the presentation. The system may include a plurality of scent producers, each of the scent producers positioned in proximity to a respective user of the presentation, where the central control unit is communicatively coupled with the local control unit of each of the scent producers, and configured to transmit to selected ones of the scent producers a respective scent track associated with the presentation and with the respective user, and to initiate activation of the selected ones of the scent producers in response to the respective scent track, to emit at least one scent according to the respective scent emission instructions, such that at least one predetermined scent is emitted to the respective user during a respective scene of the presentation. The central control unit may be further configured to synchronize timing of each of the scent producers. The central control unit may be associated with at least one of: a film projection system; a video broadcast system; a television; a set-top box; a streaming media player, a computing device; an audio medium source; a visual medium source; and/or a live performance. The scent producer may further include a plurality of valves, each of the valves configured to dispense a scent essence into a respective one of the chambers. The scent producer may further include a cam, coupled to the first motor; a push member; a rocker; and a piston, where the first motor is driven so as to rotate the cam to drive the piston via the push member and the rocker, so as to depress the selected actuator to force at least a portion of the scent essence in the respective chamber to exit via the selected actuator port. The chambers may be disposed radially about a longitudinal axis of the body. The scent producer may further include a plurality of receptacles, each one of the receptacles associated with a respective chamber and to receive a respective actuator, where each of the actuators comprises a respective fin, and each of the receptacles comprises a respective slot, the respective fin configured to engage within a respective slot so as to maintain a direction of the respective actuator port. The housing may include a cover, and a shell, whereby the cover is configured to engage securely with the shell so as to encase the body, and where the nozzle extends through a wall of the cover, providing a pathway thereto from the selected actuator port to the external environment. The body may be a circular body, where the second motor is a rotation motor configured to rotate the chambers, so as to align the selected actuator port of the selected actuator respective of the selected chamber, with the nozzle. The body may be a linear body, where the second motor is configured to translate the chambers, so as to align the selected actuator port of the selected actuator respective of the selected chamber, with the nozzle. Each of the scent producers may be secured to an articulating arm of a seat, such that the scent producer is adjustable between an inactive position, in which the scent producer is not engaged with a user of the seat, and an active position, in which the scent producer is positioned with the nozzle facing a user of the seat.

In accordance with a further aspect of the present invention, there is thus provided a method for generating timing and location coordinated scents linked to an audio/visual presentation. The method includes the step of positioning at least one electronically controlled scent producer in proximity to a user of the presentation. The scent producer includes a moveable body, and a housing, configured to encase the body and including a nozzle extending therethrough. The body includes: a plurality of chambers; a plurality of actuators, respective of the chambers; a first motor; a second motor; and a local control unit. The chambers are disposed along a base on the interior of the body, each of the chambers configured to receive a respective scent essence. Each of the actuators includes an actuator port, configured to be aligned in a selected direction in relation to the body. The first motor is configured to drive the application of pressure in a selected actuator so as to induce emission of a scent essence through the actuator port. The second motor is configured to drive the displacement of at least a portion of the body. The local control unit, responsive of scent emission instructions, is configured to selectively activate the second motor to displace the body, so as to align with the nozzle a selected actuator port of an actuator respective of the selected chamber, and configured to selectively activate the first motor to induce emission of the scent essence contained in the selected chamber through the selected actuator port, so as to produce a scent emission directed to the external environment through the nozzle. The method further includes the step of receiving at the scent producer a scent track associated with the presentation, the scent track including scent emission instructions including scent identification information and associated timing information. The method further includes the step of initiating an activation of the scent producer in response to the scent track, to emit at least one scent according to the scent emission instructions, such that at least one predetermined scent is emitted to the user during a respective scene of the presentation. The step of positioning at least one electronically controlled scent producer in proximity to a user of the presentation may include positioning a plurality of scent producers, each positioned in proximity to a respective user of the presentation; the step of receiving at the scent producer a scent track associated with the presentation may include receiving at selected ones of the scent producers a respective scent track associated with the presentation and with the respective user; and the step of initiating an activation of the scent producer in response to the scent track, may include initiating activation of the selected ones of the scent producers in response to the respective scent track, to emit at least one scent according to the respective scent emission instructions, such that at least one predetermined scent is emitted to the respective user during a respective scene of the presentation. The method may further include the step of synchronizing timing of each of the scent producers. The scent track may be received from at least one of: a film projection system; a video broadcast system; a television; a set-top box; a streaming media player; a computing device; an audio medium source; a visual medium source; and/or a live performance. Positioning a plurality of scent producers may include securing each of the scent producers to an articulating arm of a seat, such that the scent producer is adjustable between an inactive position, in which the scent producer is not engaged with a user of the seat, and an active position, in which the scent producer is positioned with the nozzle facing a user of the seat.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

Figure 1A:
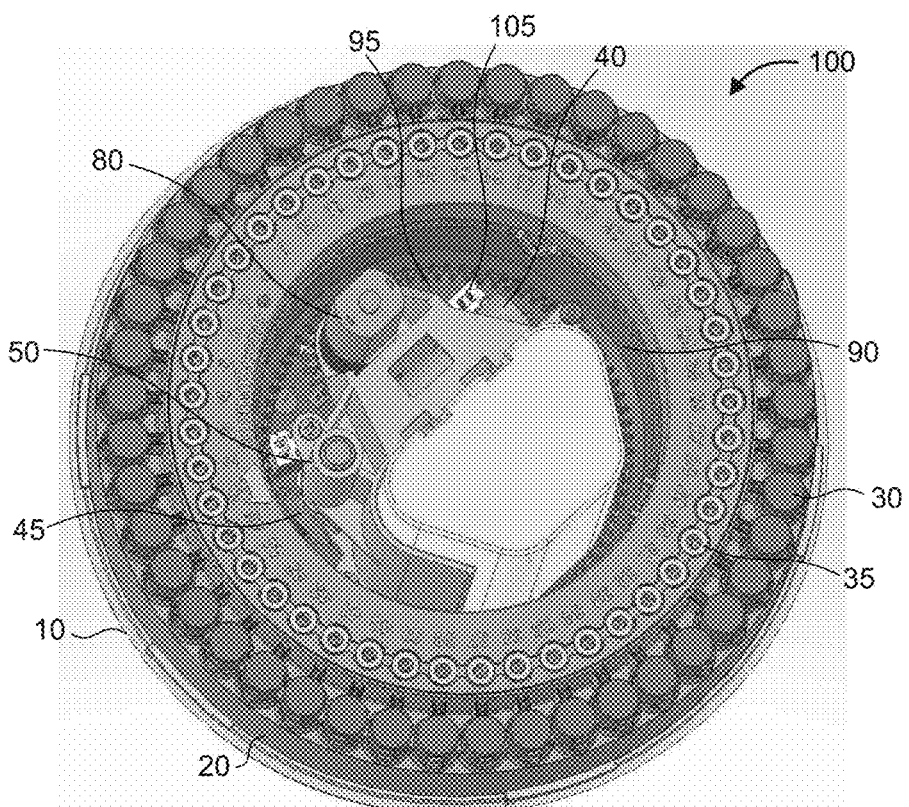
FIG. 1A is a perspective view illustration of an electronically controlled scent producer with a cover removed, constructed and operative in accordance with an embodiment of the present invention.

The present invention will be apparent from the following detailed description, which proceeds with reference to the accompanying drawings, wherein the same references relate to the same elements.

In its broadest aspects, the present invention is directed at delivery of scents associated with the appropriate scenes of a presentation, for enhancing the listening or watching experience of a spectator, listener or an audience of the presentation. Generally, among objects which need to be addressed for making such a venture successful are: homogeneous distribution of scents; timing and synchronization of scents; prevention of interference of scents, whether inside the device or in the air; environmental impact, e.g., the relationship of the movie theatre and air-conditioning to the scent provision; versatility and amount of scents; required infrastructure; cost; and efficiency.

Some of the difficulties involve: the interference of different scents with each other within the device; persistence of scents in the air while a new scent is to be provided; long term persistence of a scent; achieving precise synchronization of the scents with the relevant frame(s) of the movie ("event"); automation of the scenting system; simultaneous timing of the scents in all seats in the movie theatre; the impact of the air-conditioning system on the distribution of the scents; versatility and number of different scents to be available for a certain movie; removal of scents from a distribution system throughout the movie theatre; complicated, and expensive, infrastructure of the system; time required to adapt a movie theatre for scents; cost of the system infrastructure; requirement that the scents can only be provided in such a properly prepared movie theatre; and the prevention of scents' cloud of molecules to enter directly to the nose, to avoid user discomfort.

Distribution of a large amount of scent, e.g., to fill a theatre hall, results in the scent molecules exhibiting persistence, i.e., it takes a relatively long duration of time for the scent to "fade out". Until the scent has successfully "faded out", the introduction of any new scent results in an undesirable mix of scents.

The present invention overcomes such challenges by providing a novel electronically controlled scent producer, along with a system and method for generating timing and location coordinated scents linked to an audio/visual presentation. The system may include a plurality of scent producers, each positioned in proximity to a respective user of the presentation, for example being secured to a seat of a user watching a video broadcast or streaming at a movie theater or home theater. Each scent producer receives a respective scent track associated with the presentation and with the respective user, the scent track including scent emission instructions with timing information and associated scent identification information. Selected scent producers are activated in response to the respective scent track, to emit one or more predetermined scents that are synchronized with respective scenes of the presentation, according to the respective scent track. Accordingly, the system and method of the present invention may produce controlled scents at each of a plurality of user locations, such as respective seats of a theater or performance venue, without requiring the provision and deployment of dedicated piping systems or similar centrally operating scent production infrastructure, with associated complexity and costs. The present invention may further diminish the need for cleaning and maintenance of such piping systems. The system and method may be deployed in any suitable venue or presentation setting with minimal assembly, without requiring considerable outlays or time investments for adapting the venue to accommodate scent production and distribution, and involving minimal interference with existing infrastructure at the venue such as heating and air conditioning systems. The scent producer of the present invention may provide versatility and robustness, such as the ability to produce a wide variety of scents in a short period of time, where different scents can be added or removed in accordance with the particular audio/visual presentation. The emitted scents may be characterized with low degree of persistence, such that the emission of a first scent minimally interferes with the emission of a subsequent scent emitted shortly thereafter, providing the user with an enhanced olfactory sensation and improved experience of the presentation. Furthermore, the emission of the scents may be adapted to the particular preferences or requirements of each user, such as to limit or to increase the scent intensity, or to adjust the distance with respect to the nose or face of the user so as to avoid user discomfort.

For a better understanding of certain embodiments and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of exemplary embodiments only, and are presented in the cause of providing what is believed to be a useful and readily understood description of the principles and conceptual aspects. In this regard, no attempt is made to show structural details in more detail than is necessary for a fundamental understanding, the description taken with the drawings making apparent to those skilled in the art how the several forms may be embodied in practice.

The terms "presentation" and "audio/visual presentation" as used herein refers to any form of audio or visual content that may be presented to and consumed by one or more individuals (users). Examples of a such presentations may include, but are not limited to: a film; a television show; a commercial or advertisement; a video clip; an audio clip; a song; a musical performance; a recorded audio or video performance (e.g., played on a streaming platform or from a physical recording medium); a live performance; a live audio or video performance (e.g., played during a live concert, play, or show); a section of visual information including written text and/or image content, such as in the form of a book, an article or other passage of a magazine, journal, newspaper publication, or website; a drawing; a photograph, a cartoon; a gallery presentation; a lecture; a lesson; a business presentation; and the like.

The term "scene" is used herein to refer to a particular portion or section of the presentation. An example of a scene may include, but is not limited to: a scene or act of a film, or television show; a frame or series of frames of a video or audio clip; a selected duration or segment of a song or audio recording or performance; a sentence, paragraph, page, or chapter of text content; a slide or frame of a drawing sequence; a selected duration or segment of a lecture or presentation; and the like.

The term "user" herein refers to an individual upon which the method or system of the present invention is operated on, such as a person to whom a scent is selectively emitted. The subject may be any living entity, including a person, human or animal.

The term "scent" is used herein to broadly refer to a particular combination of chemical compounds at any concentration that is capable of being perceived by a person using his/her sense of smell, such as a fragrance or an odor, regardless of whether the perception is perceived as being pleasant or unpleasant.

The terms "scent-producer" and conjugations thereof such as scent production, in the context of the invention herein, refers to emitting, ejecting, delivering, discharging, releasing, distributing and the like, of a readily made scent, rather than manufacturing, creating, of making the scent.

The term "motor" is used herein in its broadest sense and may include any actuator, e.g., an electric driver, a magnetic solenoid, or a piezoelectric actuator, featuring any suitable motion, e.g., rotational or linear.

Figure 1B:
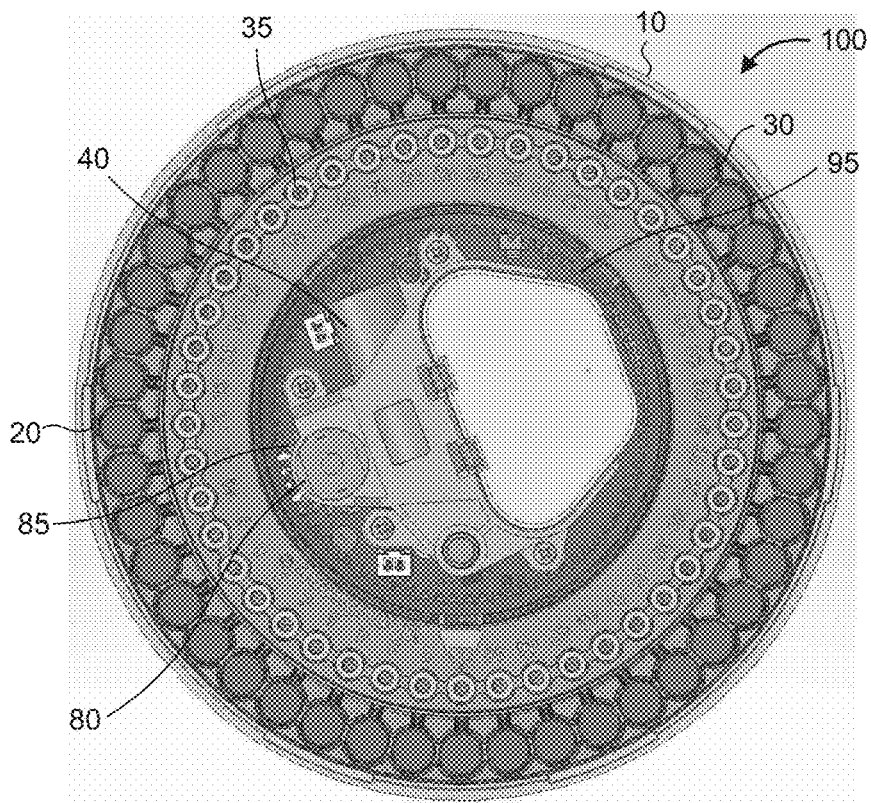
FIG. 1B is a top view illustration of the electronically controlled scent producer of FIG. 1A, constructed and operative in accordance with an embodiment of the present invention.
Figure 1C:
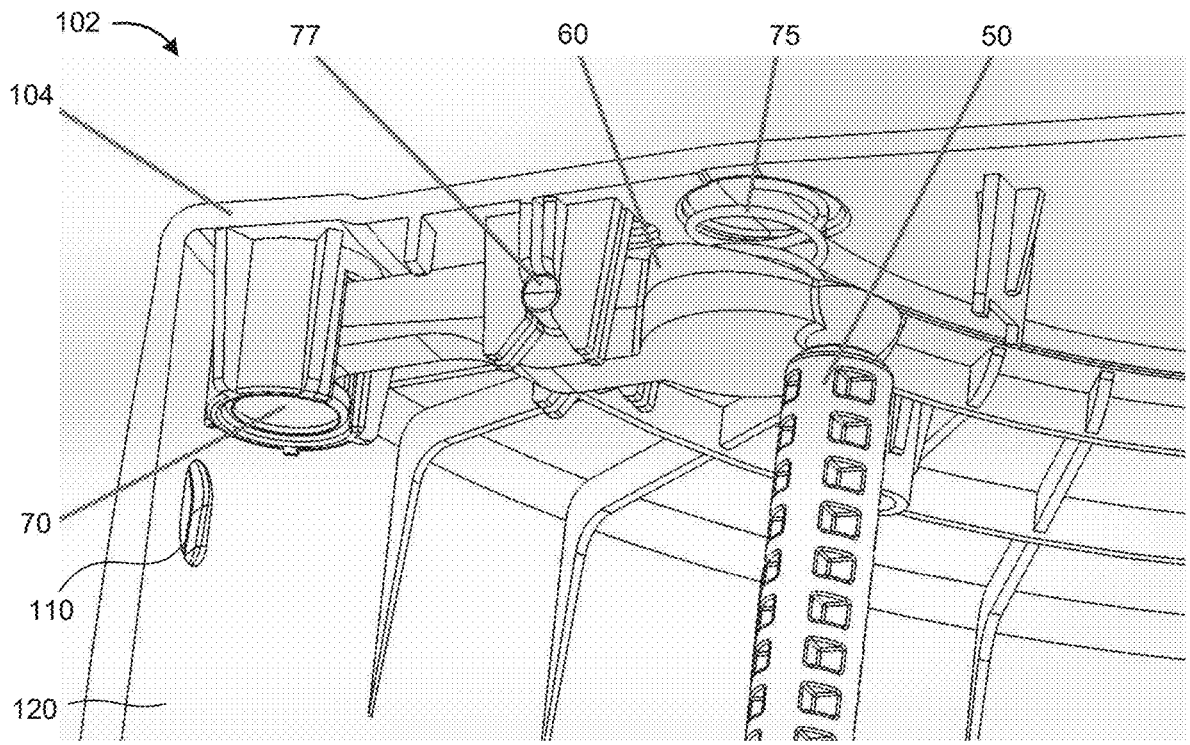
FIG. 1C is an inner perspective view illustration of an exemplary housing of the electronically controlled scent producer of FIG. 1A, constructed and operative in accordance with an embodiment of the present invention.

Reference is now made to FIGS. 1A, 1B and 1C. FIG. 1A is a perspective view illustration of an electronically controlled scent producer, generally referenced 100, with a cover removed, constructed and operative in accordance with an embodiment of the present invention. FIG. 1B is a top view illustration of the electronically controlled scent producer 100 of FIG. 1A. FIG. 1C is an inner perspective view illustration of an exemplary housing 102 of the electronically controlled scent producer 100 of FIG. 1A. Electronically controlled scent producer 1 includes a local control unit 105; a bottom tray 10; a body 20; a plurality of actuators 30; a plurality of duckbill valves 35; a first motor 40, also referred to as a whiff motor 40; a cam 45; a push member 50, which may be implemented as a push rod; a rocker 60; a piston 70; a spring 75; a hinge 77; a second motor 80, also referred to as a rotation motor 80; a cog wheel 85; an inner wall 90 of body 20 with internal gear 95; and a housing 102. Housing 102 includes a cover 104 and a lower shell 310. In one example, rotation motor 80 is a step motor. Body 20 sits on bottom tray 10, and is set to freely rotate within a lower shell 310, which lower shell 310 described further below in relation to FIG. 3. Rotation motor 80 is secured to lower shell 310, and rotates about an axis of rotation motor 80 responsive to local control unit 105, so as to rotate cog wheel 85. Teeth of cog wheel 85 mesh with internal gear 95 of body 20, and as a result body 20 rotates within lower shell 310 responsive to control unit 105. Body 20 may be provided with bearings, such as ball bearings, and lower shell 310 may be provided with a track, to ensure smooth rotation of body 20 about an inner floor of lower shell 310, and on a floor provided by the lower shell. The bearing may be provided on a bottom surface (not shown) of bottom tray 10.

Whiff motor 40 is secured to the lower shell and rotates responsive to control unit 105. Cam 45 is connected to a rotating member of whiff motor 40 and rotates therewith responsive to control unit 105. Cam 45, during a portion of a single rotation, engages with push member 50 to drive rocker 60 so as to drive piston 70 to depress a respective one of actuators 30, and then disengages, responsive to spring 75. Hinge 77, upon which rocker 60 partially rotates, and which secures rocker 60 to cover 104, and spring 75, cooperate so that in response to push rod 50 driven in a direction towards cover 104 by cam 45, piston 70 is driven away from cover 104 so as to drive piston 70 towards a respective actuator 30, so as to force a portion of scent essence contained therein to exit the actuator 30 as an emitted scent. When push rod 50 is not driven towards cover 104 by cam 45, push rod 50 is driven back towards cam 45 by spring 75, thereby withdrawing piston 70 towards cover 104 so as not to engage with the respective actuator 30. Nozzle 110 proceeds from an inner wall 120 of cover 104 through to an outer wall of cover 104. Actuators 30 may each be implemented as an aerosol actuator or an atomizer, without limitation.

Figure 2A:
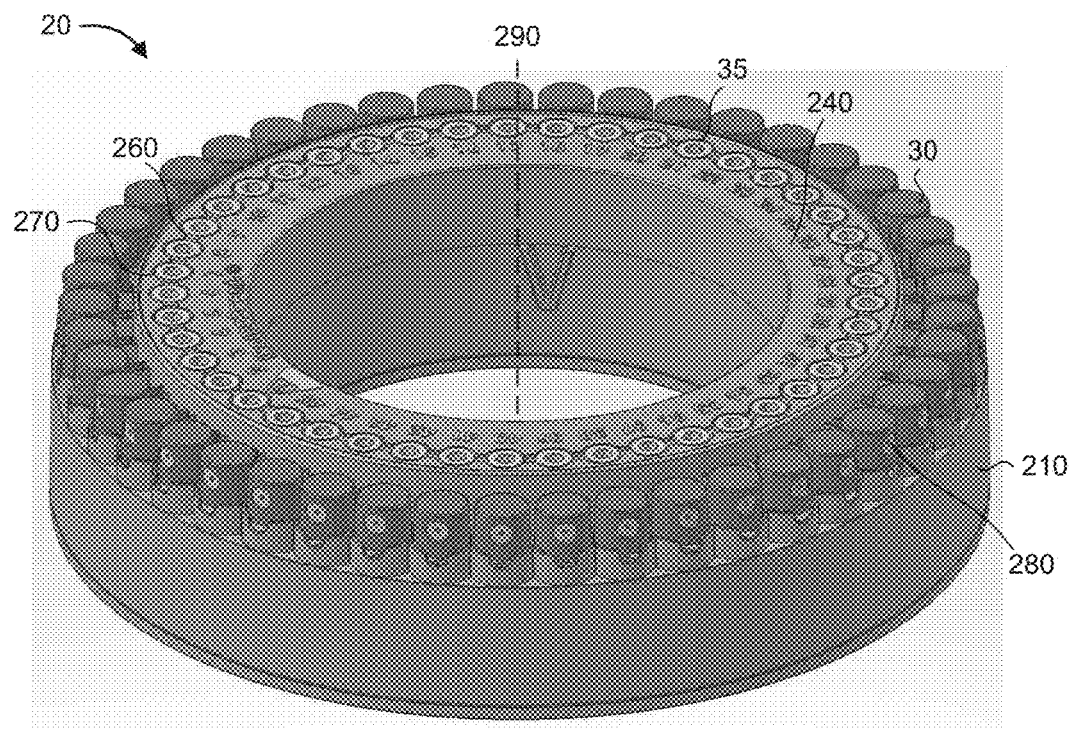
FIG. 2A is a perspective view illustration of an exemplary body of the electronically controlled scent producer of FIG. 1A, constructed and operative in accordance with an embodiment of the present invention.
Figure 2B:
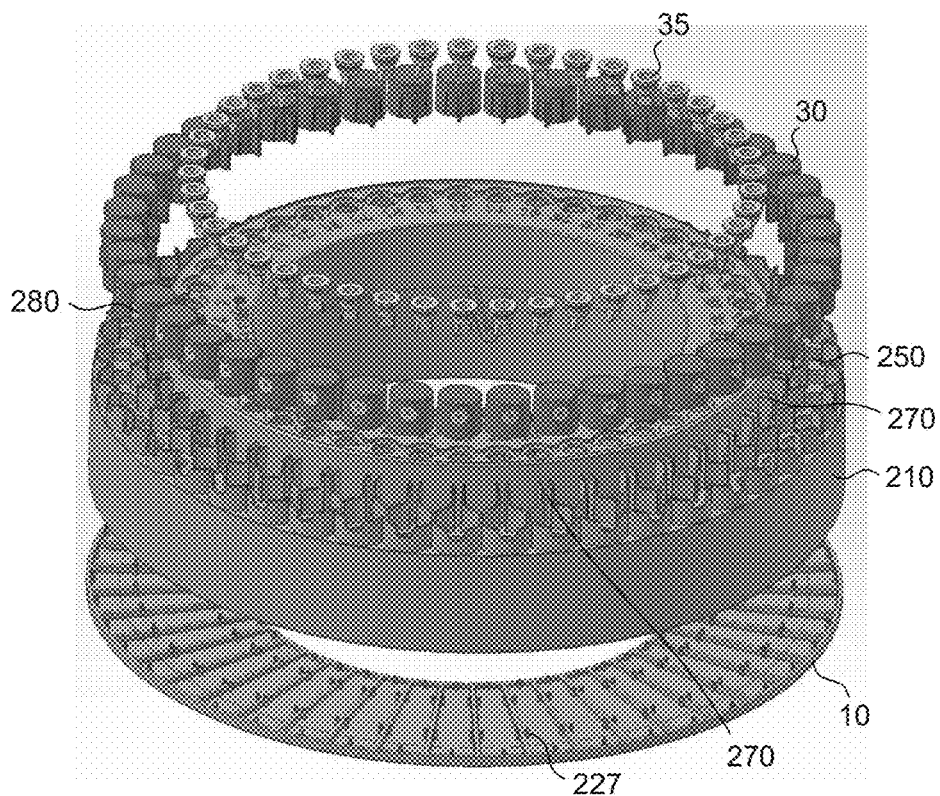
FIG. 2B is an exploded view illustration of the exemplary body of FIG. 2A, constructed and operative in accordance with an embodiment of the present invention.
Figure 2C:
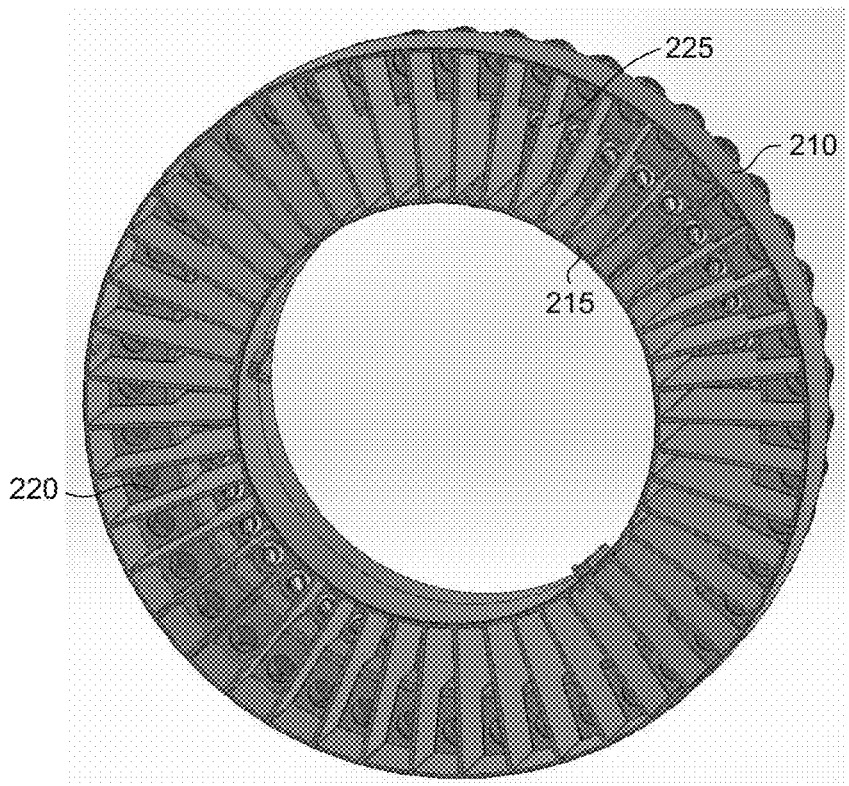
FIG. 2C is a perspective bottom view illustration of the exemplary body of FIG. 2A, constructed and operative in accordance with an embodiment of the present invention.
Figure 2D:
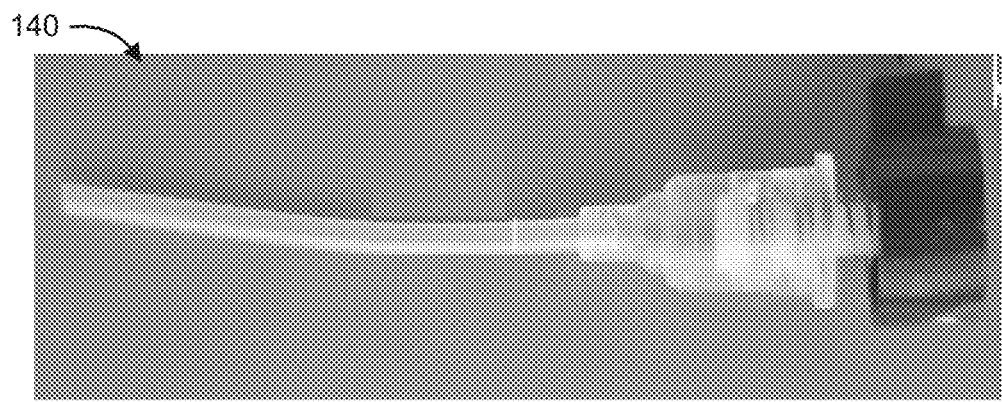
FIG. 2D is a photographic illustration of an exemplary actuator of the electronically controlled scent producer of FIG. 1A, constructed and operative in accordance with an embodiment of the present invention.

Reference is now made to FIGS. 2A, 2B, 2C and 2D. FIG. 2A is a perspective view illustration of an exemplary body 20 of the electronically controlled scent producer 100 of FIG. 1A, constructed and operative in accordance with an embodiment of the present invention. FIG. 2B is an exploded view illustration of the exemplary body 20 of FIG. 2A. FIG. 2C is a perspective bottom view illustration of the exemplary body of FIG. 2A. FIG. 2D is a photographic illustration of an exemplary actuator 30 of the electronically controlled scent producer 100 of FIG. 1A. Body 20 includes: a base 210; a plurality of chambers 220; a flange 240; a plurality of receptacles 250; and a plurality of slots 270. Actuators 30 each exhibit an actuator port 280 and a fin 260, with fin 260 sized and dimensioned to fit within a respective slot 270 so as to maintain a direction of port 280. In the example shown, fin 260 and slot 270 cooperate to point port 280 radially outward from a longitudinal axis 290 of body 20.

Flange 240 is radially displaced from longitudinal axis 290 and provides support for duckbill valves 35 radially disposed at equal angles about longitudinal axis 290. Base 210 comprises a plurality of chambers 220, each chamber 220 for receipt of a scent essence, which may be provided through a respective duckbill valve 35. The term "scent essence" as used herein refers to a fixed concentration of chemical compounds representing a particular fragrance or odor (scent), which is typically (but not necessarily) provided in liquid form, such that the emission of the scent essence through the actuator port (described further hereinbelow) provides an emitted scent in the form of a mist or vapor of the scent essence, which is capable of olfactory perception by a user.

Chambers 220 are separated from each other by a respective radial wall 225 extending from an inner band 215 to an inner wall 217 of base 210. Each of inner band 215 and inner wall 217 of base 210 describe a substantially circular band of material at a predetermined radial distance from longitudinal axis 290, with the radial distance of inner wall 217 of base 210 being greater than the radial distance of inner band 215, and in cooperation with respective radial walls 225 thereby defining chambers 220. Base 210 is secured to bottom tray 10, which exhibits matching assemblies 227 to securely mate with each radial wall 225. In one non-limiting example, 45 chambers 220 are provided, although scent producer 100 may generally include any number of chambers 220.

Each chamber 220 may receive a unique scent essence, or multiple chambers 220 may receive a common scent essence. Each receptacle 250 mates with a respective chamber 220, and is further arranged to receive a respective actuator 30. Depressing a respective actuator 30, via piston 70 (as described hereinabove in relation to FIGS. 1A, 1B, 1C), provides pressure to the respective chamber 220, thus forcing a portion of the scent essence contained therein to exit via the respective actuator port 280 as a scent, e.g., in the form of a mist or vapor. Scent essence is refilled through the respective duckbill valve 35, which as indicated above is in communication with the respective chamber 220.

As shown in FIG. 2D, a sample actuator 30 may exhibit a spring pump with a tube for drawing the scent essence.

Scent producer 100 has been particularly described in an exemplary embodiment as having a circular body, although it is understood that this is not meant to be limiting in any manner. For example, scent producer 100 may be embodied by a circular shaped body 20 that is at least partially rotatable with respect to the housing 102 (i.e., the shell 310 and/or cover 102), where second motor 80 is a rotation motor configured to rotate chambers 220 and/or actuators 30 so as to align the actuator port 280 of a selected actuator 30 with the nozzle 110. Alternatively, scent producer 100 may be embodied by a linear (e.g., rectangular shaped) body 20 that is at least partially displaceable with respect to the housing 102 (i.e., the shell 310 and/or cover 102), where second motor 80 is configured to translate or linearly displace chambers 220 and/or actuators 30 so as to align the actuator port 280 of a selected actuator 30 with the nozzle 110. Other shapes may similarly be utilized without exceeding the scope.

Figure 3:
FIG. 3 is a perspective view illustration of an exemplary electronically controlled scent producer with assembled housing, constructed and operative in accordance with an embodiment of the present invention.

Reference is now made to FIG. 3, which is a perspective view illustration of an exemplary electronically controlled scent producer 100 with assembled housing 102, constructed and operative in accordance with an embodiment of the present invention. FIG. 3 depicts scent producer 100 with cover 104 assembled to lower shell 310.

Cover 104 meets with lower shell 310 so as to encase body 20 assembled to bottom tray 10, and is secured thereto. Nozzle 110 is a pipe or tube adapted to direct an external flow of a scent contained in a chamber 220 of scent producer 110. In particular, nozzle 110 extends from an inner wall 120 of cover 104 (see FIG. 1C) through to an outer wall 320 of cover 104, and thus provides a path to the surrounding environment for an output (i.e., an emitted scent) of a respective port 280 of an actuator 30 aligned with nozzle 110. While nozzle 110 has been described as being within cover 104, this is not meant to be limiting in any way, as nozzle may alternatively be provided as a portion of body 20. Cover 104 may be provided integrally with body 20, or as a separate element, without limitation.

Figure 4:
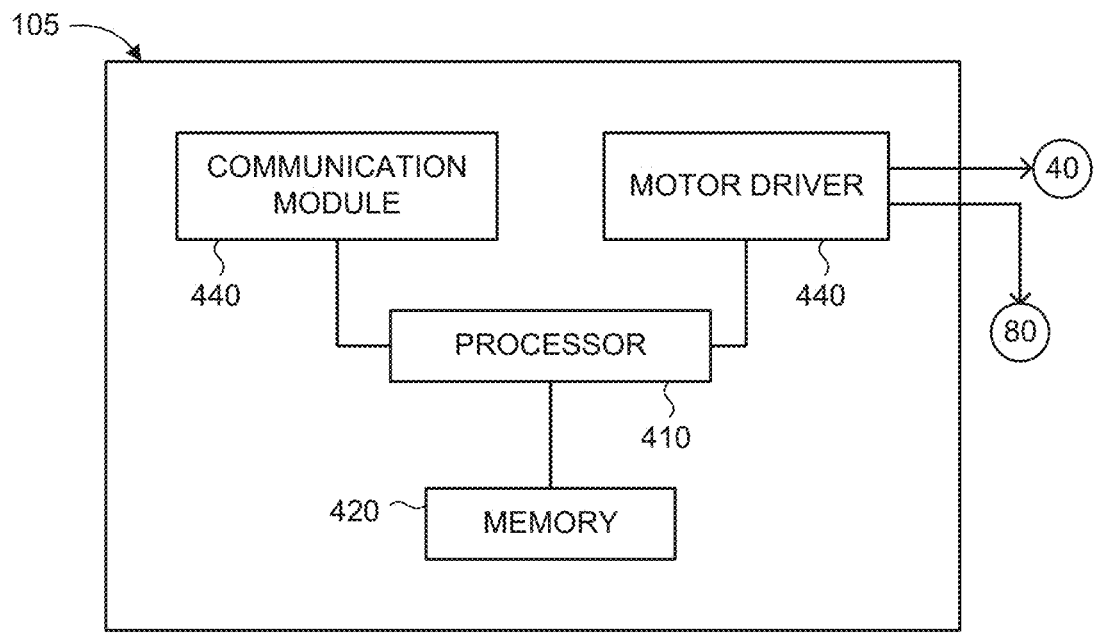
FIG. 4 is a block diagram of an exemplary local control unit of an electronically controlled scent producer, constructed and operative in accordance with an embodiment of the present invention.

Reference is made to FIG. 4, which is a block diagram of an exemplary local control unit 105 of an electronically controlled scent producer 100, constructed and operative in accordance with an embodiment of the present invention. Local control unit 105 includes a local processor 410, also denoted as local main processor (LMP) 410, a memory 420, a communications module 430, and a motor driver 440. Memory 420 is loaded with electronically readable instructions, which when read by LMP 410, directs LMP 410 to perform the functions described herein. LMP 410 is in communication with each of memory 420, communications module 430 and motor driver 440. Each of whiff motor 40 and rotation motor 80 are coupled to respective outputs of motor driver 440 and are responsive thereto. Motor driver 440 may be implemented as multiple motor drivers, each driving a respective one of whiff motor 40 and rotation motor 80 without exceeding the scope. Communications module 430 may be implemented by any wireless communication module, e.g. Wi-Fi, Bluetooth, Thread or ZigBee, without limitation, or by an Ethernet module for wired communication.

Scent producer 100 may optionally include and/or be associated with additional components not shown in the Figures, for enabling implementation of the disclosed subject matter. For example, scent producer 100 may include a power source (not shown), which may be embodied by an onboard rechargeable cell mounted in a portion of body; by an external power supply; or any combination thereof.

Figure 5:
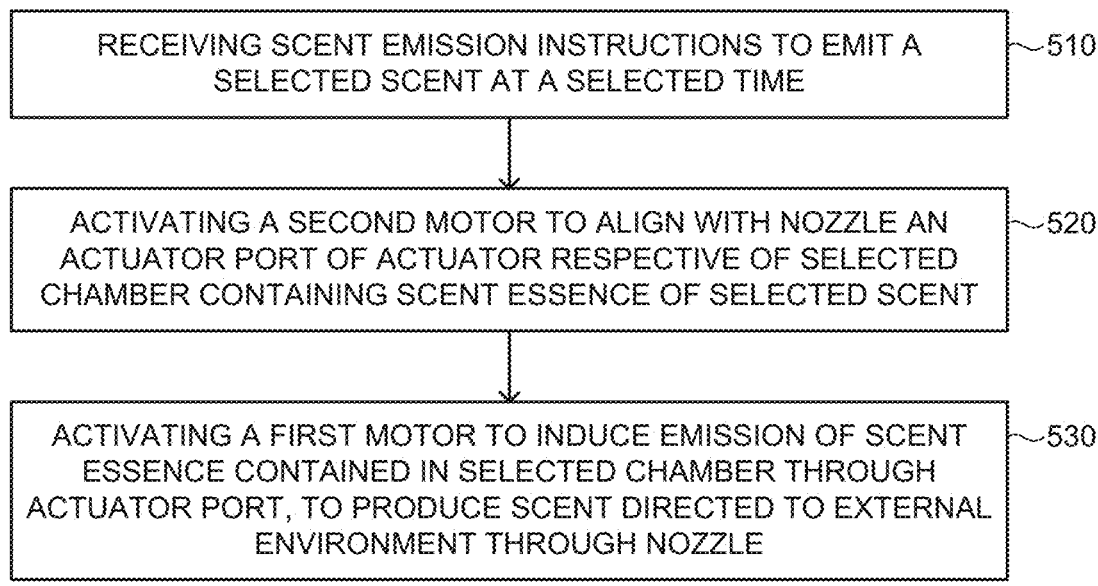
FIG. 5 is a flow diagram of an exemplary operation of a local control unit of an electronically controlled scent producer to produce a scent, operative in accordance with an embodiment of the present invention.

Reference is made to FIG. 5, which is a flow diagram of an exemplary operation of a local control unit (105) of an electronically controlled scent producer (100) to produce a scent, operative in accordance with an embodiment of the present invention. In stage 510, scent emission instructions to emit a selected scent at a selected time is received. Referring to FIGS. 1A, 2A and 4, local control unit 105 of scent producer 100 receives scent emission instructions, such as via communications module 430. The scent emission instructions include an indication of one or more scents to be emitted from scent producer 100, the scent associated with a respective scent essence contained in a particular chamber 220 of scent producer 100, and timing information relating to when the scents should be emitted.

In stage 520, a second motor is activated to align with the nozzle an actuator port of an actuator respective of the selected chamber containing the scent essence of the selected scent. Referring to FIGS. 1A, 2A and 4, local processor 410 of local control unit 105 directs motor driver 440 to drive second motor 80 to rotate (or translate) chambers 220, so as to align the actuator port 280 of the respective actuator 30 of the particular chamber 220 containing the scent essence of the scent to be emitted, with nozzle 110. For example, second motor 80 may rotate a predetermined number of steps, which rotates cog wheel 85 and internal gear 95 so as to rotate rotating tray 90, to align the actuator port 280 of actuator 30 of the particular one of chambers 220, with nozzle 110. Thus, the actuator port 280 associated with the particular chamber 220 containing the particular scent essence is aligned with nozzle 110, therefore establishing a flow pathway for a scent emission to the external environment. In the event of a linear layout, second motor 80 translates the chambers 220, e.g. by translating body 20, so as to align the respective actuator port 280 of the associated actuator 30 of the particular one of chambers 220, with nozzle 110.

In stage 530, a first motor is activated to induce emission of the scent essence contained in the selected chamber through the actuator port, to produce a scent directed to the external environment through the nozzle. Referring to FIGS. 1A, 2A and 4, local processor 410 of local control unit 105 directs motor driver 440 to drive first motor 40, so as to induce emission of the scent essence contained in the selected chamber. In particular, activation of first motor 40 rotates cam 45, which drives push member 50 towards cover 104. Rocker 60, engaged with cover 104 by hinge 77, translates the drive of push member 50 into pressure on actuator 30 of the particular chamber 220, thereby inducing emission of the scent essence contained in the chamber 220 to exit via the actuator port 280 that is aligned with nozzle 110, resulting in the emission of a scent to the external environment through nozzle, such as a scent cloud in the form of a mist or vapor, that can be perceived by a user.

An electronically controlled scent producer 100 of the disclosed embodiments may find particular application in a venue or setting associated with an audio/visual presentation, such as a theater (e.g., a movie theater). For example, a plurality of scent producers may be fixedly or removably mounted to respective seats in the theater, and arranged in proximity to an occupant of the seat, such that one or more scents emitted from the scent producer 100 will be directed to the seat occupant during the presentation, such as synchronized with one or more selected scenes of the presentation.

Figure 6A:
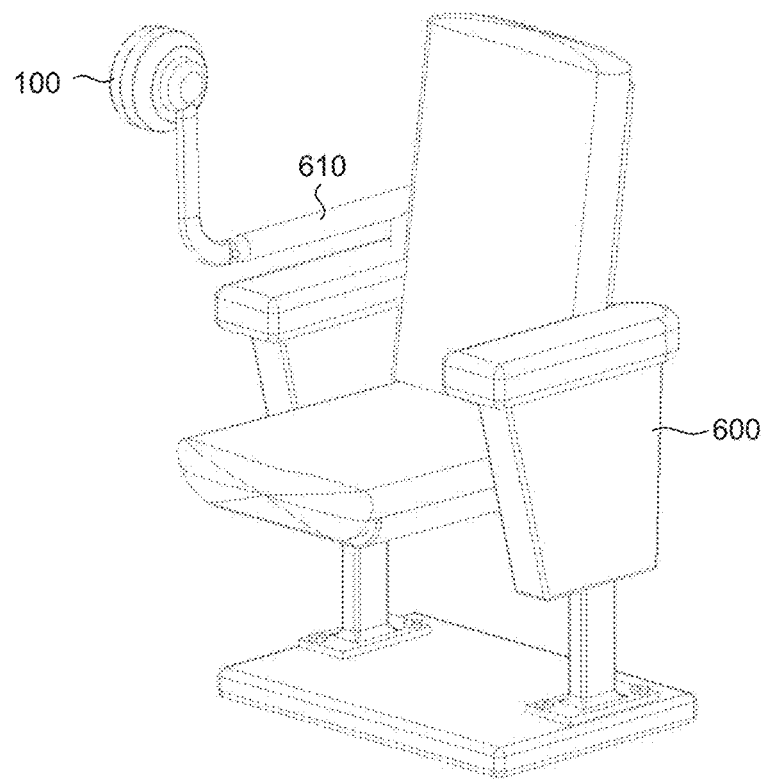
FIG. 6A is a perspective view illustration of a seat with an articulating arm securing an exemplary electronically controlled scent producer in an inactive position, constructed and operative in accordance with an embodiment of the present invention.

Reference is now made to FIG. 6A, which is a perspective view illustration of a seat, referenced 600, with an articulating arm 610, securing an exemplary electronically controlled scent producer 100, in an inactive position, constructed and operative in accordance with an embodiment of the present invention. Scent producer 100 may be mounted to a distal end of an articulating arm 610 of seat 600 (e.g., which may be separate from but adjacent to a seat armrest), where the articulating arm 610 may be characterized by degrees of freedom in one or more axis of motion, enabling adjustment of the position and orientation of the mounted scent producer 100 (e.g., by panning, tilting, swiveling the arm 610 or portions thereof). For example, scent producer 100 may be brought to an inactive position by manipulating articulating arm 610 (i.e., along one or more axes of motion) such that scent producer 100 faces away from seat 600 and arm 610 is positioned sufficiently away from the seat body so as not to interfere with the entry or exiting of a user to or from seat 600. Scent producer 100 may be fixedly mounted to articulating arm 610, i.e., such that scent producer 100 cannot be easily removed therefrom, or removably mounted to facilitate removal and reassembly (e.g., on a different seat, at the same or different venue).

Figure 6B:
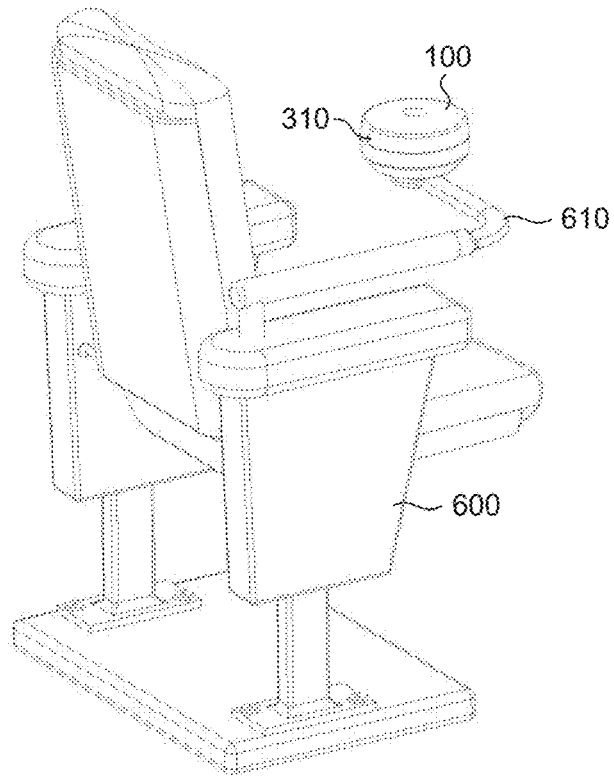
FIG. 6B is a perspective view illustration of a seat with an articulating arm securing an exemplary electronically controlled scent producer in an active position, constructed and operative in accordance with an embodiment of the present invention.

Reference is made to FIG. 6B, which is a perspective view illustration of seat 600 with an articulating arm 610, securing an exemplary electronically controlled scent producer 100, in an active position, constructed and operative in accordance with an embodiment of the present invention. Scent producer 100 may be brought to an active position, in which scent producer 100 is ready to be activated to emit one or more scents in conjunction with a presentation at the theater, by manipulating articulating arm 610 (i.e., along one or more axes of motion) such that scent producer 100 faces toward a user of seat 600, with nozzle 110 of scent producer 100 directed toward the nose of the user. For example, articulating arm 610 is configured and dimensioned such that scent producer 100 is situated approximately at a predetermined distance relative to the nose (or nostrils) of a user occupying seat 600. Multiple seats 600 in a theater (or other presentation setting) may be configured with respective articulating arms on which respective scent producers 100 are mounted, in accordance with the needs and requirements of the particular presentation.

According to an embodiment of the present invention, a system for generating timing and location coordinated scents linked to an audio/visual presentation is provided. The system includes at least one electronically controlled scent producer 100 of the disclosed embodiments, each scent producer 100 positioned in proximity to a user of the presentation. The system includes a central control unit, communicatively coupled with the local control unit 105 of each scent producer 100. The central control unit is configured to transmit scent emission instructions to one or more scent producers in the form of a scent track, associated with the presentation and with the respective user. The scent track includes scent identification information, relating to an indication of one or more scents to be emitted in the context of a respective scene of the presentation. The scent track further includes timing information, relating to the timing and duration of the scent emissions. The respective scent producer may be activated in response to the scent track, so as to emit at least one predetermined scent to the user during at least one respective scene of the presentation, in accordance with the scent identification information and timing information of the scent track Reference is made to FIG. 7A, which is a block diagram of an exemplary central control unit 650 of a system for generating timing and location coordinated scents linked to an audio/visual presentation, constructed and operative in accordance with an embodiment of the present invention. Central control unit 650 includes a central processor 652, also denoted as projection main processor (PMP) 652, a memory 654, and a central communications module 657. Memory 654 is loaded with electronically readable instructions, which when read by PMP 652, directs PMP 652 to perform the functions described herein. PMP 652 is communicatively coupled with memory 654 and central communications module 657. Central communications module 657 is further communicatively coupled with the communication modules 430 (FIG. 4) of the respective scent producers 100 of the system. Communications module 657 may be implemented by any wireless or wired communication module, e.g. Wi-Fi, Bluetooth, Thread, ZigBee, Ethernet, without limitation. The system may optionally include and/or be associated with additional components not shown in the Figures, for enabling implementation of the disclosed subject matter.

Figure 7A:
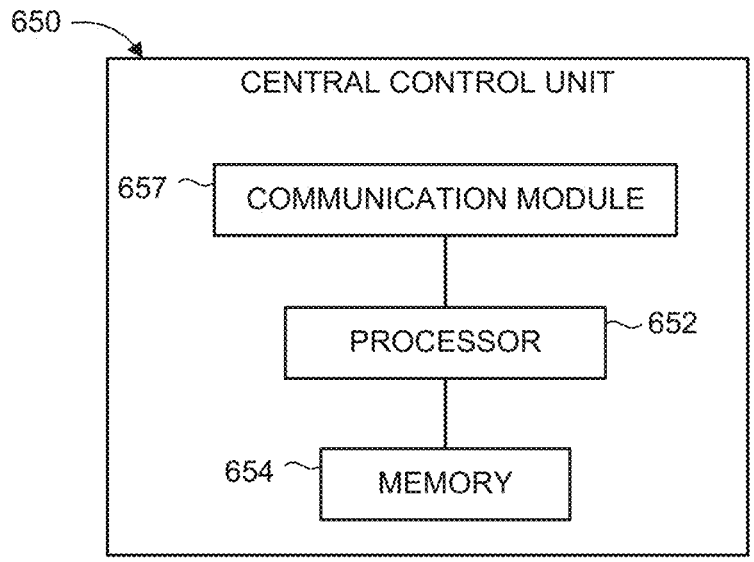
FIG. 7A is a block diagram of an exemplary central control unit of a system for generating timing and location coordinated scents linked to an audio/visual presentation, constructed and operative in accordance with an embodiment of the present invention.
Figure 7B:
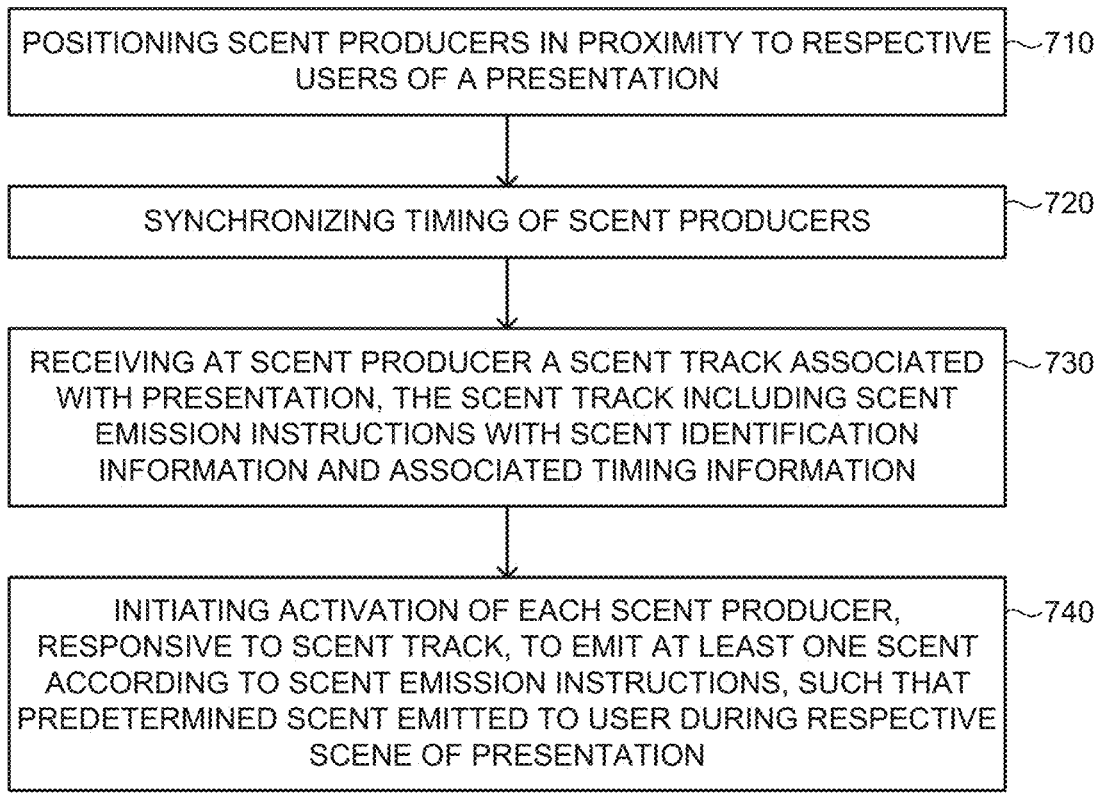
FIG. 7B is a flow diagram of an exemplary method for generating timing and location coordinated scents linked to an audio/visual presentation, operative in accordance with an embodiment of the present invention.

Reference is made to FIG. 7B, which is a flow diagram of an exemplary method for generating timing and location coordinated scents linked to an audio/visual presentation, operative in accordance with an embodiment of the present invention.

In step 710, scent producers are positioned in proximity to respective users of a presentation. Referring to FIGS. 1A, 6A, and 6B, a plurality of scent producers 100 are positioned in proximity to respective users at a venue of a presentation, such as being fixedly or removably mounted to respective articulating arms 610 of respective seats 600 in a theater. The articulating arms may be adjusted between an inactive position (FIG. 6A), to facilitate entering/exiting of a user to/from seat 600, and an active position (FIG. 6B), in which scent producer 100 is directed toward the nose of the user and ready to be activated to emit scents in conjunction with the presentation.

In optional step 720, the timing of the scent producers is synchronized. Referring to FIGS. 1A and 7A, the timing of each of the positioned scent producers is synchronized, such as by synchronizing the clocks of scent producers 100 with an internal clock of central control unit 650.

In step 730, at least one scent producer receives a scent track associated with the presentation, the scent track including scent emission instructions with scent identification information and associated timing information. Referring to FIGS. 1A and 7A, local control unit 105 of scent producer 100 receives a scent track from central control unit 650, such as via communications modules 430, 657. The scent track includes scent emission instructions including an indication of one or more scents to be emitted from scent producer 100 in conjunction with the presentation, each scent associated with a scent essence contained in a particular chamber 220. The scent emission instructions further include timing information, relating to the timing and duration of each scent to be emitted, in conjunction with the presentation.

In step 740, activation of each scent producer is initiated, responsive to the scent track, to emit at least one scent according to the scent emission instructions, such that at least one predetermined scent is emitted to the user during a respective scene of the presentation. Referring to FIGS. 1A, 6A, and 7A, PMP 652 of central control unit 650 may issue a command to each one of, or a subset of, the deployed scent producers 100, to initiate activation thereof. For example, a command may be sent simultaneously to all of the selected scent producers 100 to initiate their activation, where the command acts as a start command to commence operation in accordance with the received scent track. Each activated scent producer 100 then proceeds to emit one or more scents in accordance with the scent emission instructions of scent track, based on the indicated scents and associated timing thereof, under the direction of local control unit 105 to trigger a scent emission when applicable according to stages 520, 530 (FIG. 5). In particular, local processor 410 of local control unit 105 directs motor driver 440 to drive second motor 80 to rotate (or translate) chambers 220, so as to align the actuator port 280 of the respective actuator 30 of the particular chamber 220 containing the scent essence of the scent to be emitted, with nozzle 110 of scent producer 100 (stage 520). Subsequently, local processor 410 of local control unit 105 directs motor driver 440 to drive first motor 40, driving push member 50 which is translated by rocker 60 into pressure on actuator 30 of the particular chamber 220, inducing emission of the scent essence contained in chamber 220 to exit via actuator port 280 aligned with nozzle 110, resulting in the emission of a scent through nozzle 110 to the external environment, and its perception by the user (e.g., occupant of seat 600). In another example, each of the scent producers 100 to be activated may operate independently responsive to the respective synchronized clock and the received scent track, to activate according to the timing information contained in the received scent emission instructions, such that a central initiation command issued by central control unit 650 is not required.

The above describes a non-limiting example where a respective scent track is transmitted to a subset of the scent producers, and scent emission is coordinated based on synchronized clocks and an activation initiation trigger, however this is not meant to be limiting. In one example, clocks are not synchronized, and operation is solely responsive to a received scent track and an activation initiation. In another example, a respective scent track is sent simultaneously to a subset of scent producers, with activation of each scent producer responsive to the respective scent track controlled by the central control unit 650 of the system.

In one embodiment, each of the scent producers 100 further includes a sensor or a switch (not shown), responsive to a position of the scent producer, i.e., active position or inactive position. When the scent producer 100 is in an inactive position, LMP 410 of local control unit 105 does not enable motor driver 440 and no scent is emitted by the scent producer 100. LMP 410 may further maintain a count of each scent issued from each chamber 220, and may provide the count to PMP 652 upon request, or at the end of the scent track, so as to provide PMP 652 information regarding the fill status of each of the chambers 220. In another example PMP 652 maintains a count of each scent issued from each chamber 220 of each scent producer 100.

Figure 8:
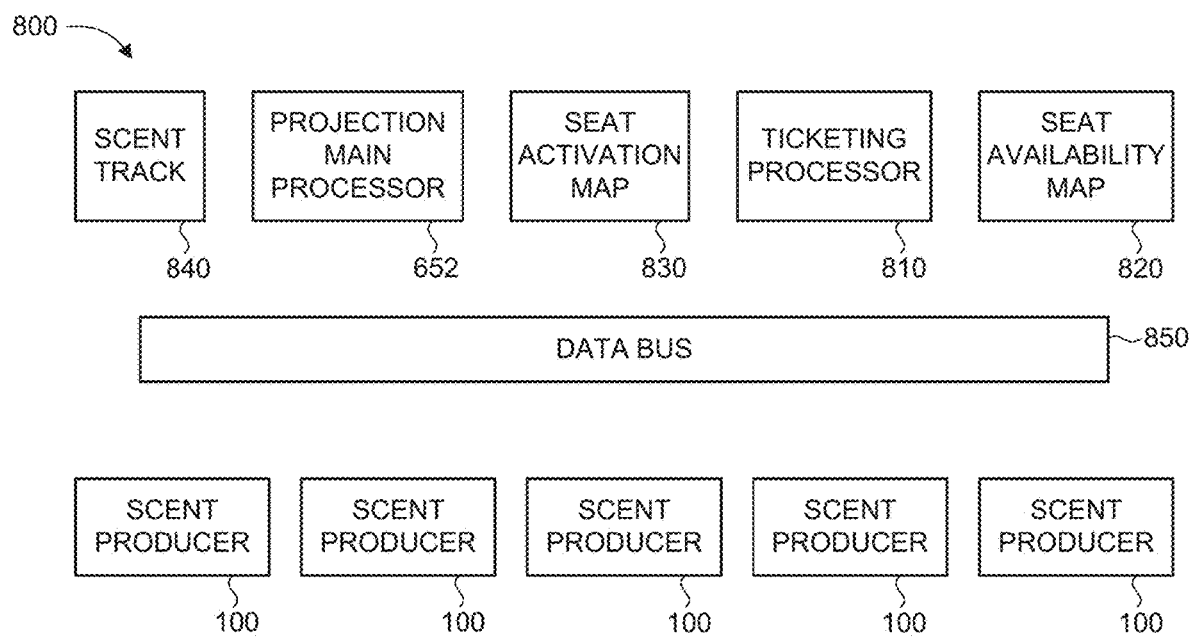
FIG. 8 is a block diagram of an exemplary configuration of a system for controlled scent production deployed in a movie theater setting, constructed and operative in accordance with an embodiment of the present invention.

Reference is made to FIG. 8, which is a block diagram of an exemplary configuration of a system for controlled scent production, generally referenced 800, deployed in a movie theater setting, constructed and operative in accordance with an embodiment of the present invention. System 800 includes: a ticketing processor 810; a seat availability map 820; PMP 652 (FIG. 7A); a seat activation map 830; a scent track 840; a data bus 850; and a plurality of scent producers 100, each associated with a respective seat (such as seat 600 depicted in FIGS. 6A and 6B). Ticketing processor 810 is in communication with PMP 652 over data bus 850. Ticketing processor 810 is in communication with seat availability map 820, and updates seat availability map 820 in accordance with ticket sales and in response to information form PMP 652. PMP 652 is in communication with each of the scent producers 100. PMP 652 further receives scent track 840 and transmits scent track 840 to each of the respective scent producers 100. PMP 652 further maintains seat activation map 830, and activates respective scent producers 100 responsive to seat activation map 830. Thus, seats which are not occupied, according to seat availability map 820, are so indicated in seat activation map 830, and the respective scent producers 100 of unoccupied seats are not enabled, or not initiated. In one example, a disable command is sent to the respective scent producers 100 of unoccupied seats, so as to prevent their operation responsive to the activation initiation of step 730 (FIG. 7B).

Seat activation map 830 is further updated by PMP 652 in response to information received from each of the respective scent producers 100. Thus, in response to information that a particular chamber 220 of one or more scent producers 100 contains insufficient scent essence, seat activation map 830 is updated so as not to trigger those scent producers 100 with insufficient scent essence in at least one chamber 220, and seat availability map 820 is updated to prevent occupancy of seats associated with scent producers 100 having insufficient scent essence in at least one chamber 220 (e.g., by not selling tickets to those seats). Alternatively, use of such seats may be allowed under restricted conditions (e.g., by providing tickets at a reduced price). Furthermore, information may be provided to an operator to refill the scent essence into the respective chambers of scent producers, as required. Seat information may be provided to the operator so as to simplify the refill process.

Figure 9:
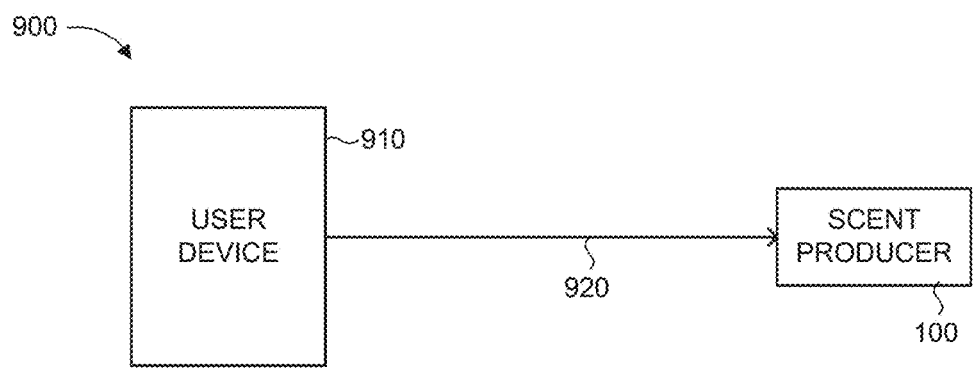
FIG. 9 is a block diagram of an exemplary configuration of a system for controlled scent production deployed in a home theater setting, constructed and operative in accordance with an embodiment of the present invention.

The above has been described in relation to a theater, however this is not meant to be limiting in any way. Central control unit 650 may be utilized with a streamer application built into a television, set-top box, streaming media player, or an application on a mobile phone, tablet or computer. Reference is made to FIG. 9, which is a block diagram of an exemplary configuration of a system, generally referenced 900, for controlled scent production deployed in a home theater setting, constructed and operative in accordance with an embodiment of the present invention. System 900 includes at least one user device 910 in communication with a scent producer 100. User device 910 may be embodied by any type of electronic device with computing and network communication capabilities, including but not limited to: a mobile computer; a desktop computer; a smartphone; a laptop computer; a netbook computer; a tablet computer; or any combination of the above. For example, user device 910 may be a television, set-top box, streaming media player, or an application on a smartphone or mobile computer. User device 910 may transmit scent emission instructions 920 to scent producer 100, and in response to the received scent instructions 920, containing scent identification information and associated timing information (as described in step 730 of FIG. 7B), scent producer 100 emits one or more scents in accordance with the scent emission instructions, under the direction of local control unit 105 to trigger a scent emission (according to stages 520, 530 of FIG. 5). User device 910 may also transmit a scent track to scent producer 100 with an activation initiation (as described in step 740 of FIG. 7B), and responsive to the activation initiation, scent producer 100 emits one or more scents in accordance with the scent emission instructions.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. An electronically controlled scent producer, comprising:
   a moveable body, and a housing, configured to encase the body and comprising a nozzle extending therethrough, the body comprising:
   a plurality of chambers disposed along a base on an interior of the body, each of the chambers configured to receive a respective scent essence;
   a plurality of actuators, respective of the chambers, each of the actuators comprising an actuator port, configured to be aligned in a selected direction in relation to the body, wherein each of the actuators further comprises a respective fin;
   a first motor, configured to drive the application of pressure in a selected actuator so as to induce emission of a scent essence through the actuator port;
   a second motor, configured to drive the displacement of at least a portion of the body;
   a local control unit including a processor and a memory, the memory containing electronically readable instructions that, when executed by the processor, direct the processor to selectively activate the second motor to displace the body responsive of scent emission instructions, so as to align with the nozzle a selected actuator port of an actuator respective of a selected chamber, and configured to selectively activate the first motor to induce emission of the scent essence contained in the selected chamber through the selected actuator port, so as to produce a scent emission directed to an external environment through the nozzle; and
   a plurality of receptacles, wherein each receptacle mates with a respective chamber of the plurality of chambers, wherein each receptacle is arranged to receive a respective actuator of the plurality of actuators, wherein each of the receptacles comprises a respective slot, wherein the respective fin of each actuator is configured to engage within a respective slot of one of the plurality of actuators so as to maintain a direction of the respective actuator port.

2. The scent producer of claim 1, further comprising a plurality of valves, each of the valves configured to dispense a scent essence into a respective one of the chambers.

3. The scent producer of claim 1, further comprising a cam, coupled to the first motor; a push member; a rocker; and a piston, wherein the first motor is driven so as to rotate the cam to drive the piston via the push member and the rocker, so as to depress the selected actuator to force at least a portion of the scent essence in the respective chamber to exit via the selected actuator port.

4. The scent producer of claim 1, wherein the chambers are disposed radially about a longitudinal axis of the body.

5. The scent producer of claim 1, wherein the housing comprises a cover, and a shell, whereby the cover is configured to engage securely with the shell, so as to encase the body, and wherein the nozzle extends through a wall of the cover, providing a pathway thereto from the selected actuator port to the external environment.

6. The scent producer of claim 5, further comprising a tray, wherein the body is secured to the tray and configured to rotate within the shell of the housing, in response to activation of the second motor.

7. The scent producer of claim 1, wherein the chambers are separated by a respective radial wall extending from an inner band to an inner wall of the base, each of the inner band and the inner wall describing a substantially circular band at a predetermined radial distance from a longitudinal axis of the body, the radial distance of the inner wall being greater than the radial distance of the inner band.

8. The scent producer of claim 1, wherein the local control unit is configured to receive a scent track, associated with an audio/visual presentation, the scent track comprising the scent emission instructions comprising scent identification information and associated timing information, the local control unit configured to trigger an activation of the scent producer to emit at least one scent according to the scent track, by selectively activating the second motor and the first motor in response to the scent track, such that at least one predetermined scent is emitted during a respective scene of the presentation.

9. A system for generating timing and location coordinated scents linked to an audio/visual presentation, the system comprising:
  at least one electronically controlled scent producer, positioned in proximity to a user of the presentation, the scent producer comprising:
  a moveable body, and a housing, configured to encase the body, the housing comprising a nozzle extending therethrough, the body comprising:
  a plurality of chambers disposed along a base on an interior of the body, each of the chambers configured to receive a respective scent essence;
  a plurality of actuators, respective of the chambers, each of the actuators comprising an actuator port, configured to be aligned in a selected direction in relation to the body, wherein each of the actuators further comprises a respective fin;
  a first motor, configured to drive the application of pressure in a selected actuator so as to induce emission of a scent essence through the actuator port;
  a second motor, configured to drive the displacement of at least a portion of the body;
  a local control unit communicatively coupled with a central control unit, the local control unit including a processor and a memory, the memory containing electronically readable instructions that, when executed by the processor, direct the processor to selectively activate the second motor to displace the body responsive of scent emission instructions, so as to align with the nozzle a selected actuator port of an actuator respective of a selected chamber, and configured to selectively activate the first motor to induce emission of the scent essence contained in the selected chamber through the selected actuator port, so as to produce a scent emission directed to an external environment through the nozzle;
  a central control unit, communicatively coupled with the local control unit, the central control unit configured to transmit to the scent producer a scent track associated with the presentation, the scent track comprising scent emission instructions comprising scent identification information and associated timing information, and configured to initiate an activation of the scent producer in response to the scent track, to emit at least one scent according to the scent emission instructions, such that at least one predetermined scent is emitted to the user during a respective scene of the presentation; and
  a plurality of receptacles, wherein each receptacle mates with a respective chamber of the plurality of chambers, wherein each receptacle is arranged to receive a respective actuator of the plurality of actuators, wherein each of the receptacles comprises a respective slot, wherein the respective fin of each actuator is configured to engage within a respective slot of one of the plurality of actuators so as to maintain a direction of the respective actuator port.

10. The system of claim 9, further comprising a plurality of scent producers, each of the scent producers positioned in proximity to a respective user of the presentation, wherein the central control unit is communicatively coupled with the local control unit of each of the scent producers, and configured to transmit to selected ones of the scent producers a respective scent track associated with the presentation and with the respective user, and to trigger activation of the selected ones of the scent producers in response to the respective scent track, to emit at least one scent according to the respective scent emission instructions, such that at least one predetermined scent is emitted to the respective user during a respective scene of the presentation.

11. The system of claim 10, wherein the central control unit is configured to synchronize timing of each of the scent producers.

12. The system of claim 9, wherein the scent producer further comprises a plurality of valves, each of the valves configured to dispense a scent essence into a respective one of the chambers.

13. The system of claim 9, wherein the scent producer further comprises a cam, coupled to the first motor; a push member; a rocker; and a piston, wherein the first motor is driven so as to rotate the cam to drive the piston via the push member and the rocker, so as to depress the selected actuator to force at least a portion of the scent essence in the respective chamber to exit via the selected actuator port.

14. The system of claim 9, wherein the chambers are disposed radially about a longitudinal axis of the body.

15. The system of claim 9, wherein the housing comprises a cover, and a shell, whereby the cover is configured to engage securely with the shell, so as to encase the body, and wherein the nozzle extends through a wall of the cover, providing a pathway thereto from the selected actuator port to the external environment.

16. A method for generating timing and location coordinated scents linked to an audio/visual presentation, the method comprising the steps of:
  positioning at least one electronically controlled scent producer in proximity to a user of the presentation, the scent producer comprising:
  a moveable body, and a housing, configured to encase the body, the housing comprising a nozzle extending therethrough, the body comprising:
  a plurality of chambers disposed along a base on an interior of the body, each of the chambers configured to receive a respective scent essence;
  a plurality of actuators, respective of the chambers, each of the actuators comprising an actuator port configured to be aligned in a selected direction in relation to the body, wherein each of the actuators further comprises a respective fin;
  a first motor, configured to drive the application of pressure in a selected actuator so as to induce emission of a scent essence through the actuator port;
  a second motor, configured to drive the displacement of at least a portion of the body;
  a local control unit including a processor and a memory, the memory containing electronically readable instructions that, when executed by the processor, direct the processor to selectively activate the second motor to displace the body responsive of scent emission instructions, so as to align with the nozzle a selected actuator port of an actuator respective of a selected chamber, and configured to selectively activate the first motor to induce emission of the scent essence contained in the selected chamber through the selected actuator port, so as to produce a scent emission directed to an external environment through the nozzle; and a plurality of receptacles, wherein each receptacle mates with a respective chamber of the plurality of chambers, wherein each receptacle is arranged to receive a respective actuator of the plurality of actuators, wherein each of the receptacles comprises a respective slot, wherein the respective fin of each actuator is configured to engage within a respective slot of one of the plurality of actuators so as to maintain a direction of the respective actuator port;

receiving at the scent producer a scent track associated with the presentation, the scent track comprising scent emission instructions comprising scent identification information and associated timing information; and initiating an activation of the scent producer in response to the scent track, to emit at least one scent according to the scent emission instructions, such that at least one predetermined scent is emitted to the user during a respective scene of the presentation.

17. The method of claim 16, wherein the step of positioning at least one electronically controlled scent producer in proximity to a user of the presentation comprises positioning a plurality of scent producers, each positioned in proximity to a respective user of the presentation, wherein the step of receiving at the scent producer a scent track associated with the presentation comprises receiving at selected ones of the scent producers a respective scent track associated with the presentation and with the respective user, and wherein the step of initiating an activation of the scent producer in response to the scent track, comprises trigger activation of the selected ones of the scent producers in response to the respective scent track, to emit at least one scent according to the respective scent emission instructions, such that at least one predetermined scent is emitted to the respective user during a respective scene of the presentation.

18. The method of claim 16, further comprising the step of synchronizing timing of each of the scent producers.

* * * * *